United States Patent
Kurose et al.

[11] Patent Number: 5,981,132
[45] Date of Patent: Nov. 9, 1999

[54] NON-MAGNETIC MONO-COMPONENT DEVELOPER

[75] Inventors: Katsunori Kurose, Amagasaki; Masahiro Anno, Sakai; Chikara Tsutsui, Nishinomiya; Minoru Nakamura, Itami, all of Japan

[73] Assignee: Minolta Co., Ltd., Osaka, Japan

[21] Appl. No.: 09/219,426

[22] Filed: Dec. 23, 1998

[30] Foreign Application Priority Data

Dec. 24, 1997 [JP] Japan ................................. 9-354880

[51] Int. Cl.$^6$ ..................................................... G03G 9/097
[52] U.S. Cl. ........................................... 430/110; 430/111
[58] Field of Search ..................................... 430/110, 111

[56] References Cited

U.S. PATENT DOCUMENTS

| | | | |
|---|---|---|---|
| 4,626,487 | 12/1986 | Mitsuhashi et al. | 430/109 |
| 5,215,849 | 6/1993 | Makuta et al. | 430/110 |
| 5,604,071 | 2/1997 | Okado et al. | 430/110 |
| 5,759,731 | 6/1998 | Hagi et al. | 430/106.6 |
| 5,776,646 | 7/1998 | Hagi et al. | 430/110 |

FOREIGN PATENT DOCUMENTS 07043930  2/1995  Japan .

*Primary Examiner*—Roland Martin
*Attorney, Agent, or Firm*—McDermott, Will & Emery

[57] ABSTRACT

1. A non-magnetic mono-component developer comprising:

toner particles containing at least a binder resin and a coloring agent and having a volume mean particle size D of 4 to 10 $\mu$m;

first inorganic fine particles having a mean primary particle size of 1 to 40 nm, the quantity of addition of the first inorganic fine particles being 0.1 to 2% by weight relative to the quantity of the toner particles;

second inorganic fine particles having a mean primary particle size of 40 to 100 nm and not less than 10 nm larger than the first inorganic fine particles, the quantity of addition of the second inorganic fine particles being 0.1 to 2.5% by weight relative to the quantity of the toner particles, the total quantity of addition of the first and second inorganic fine particles being 0.8 to 3% by weight relative to the quantity of the toner particles; and third inorganic fine particles having a mean primary particle size of 100 nm to 1000 D/16 nm and not less than 10 nm larger than the second inorganic fine particles, the quantity of addition of the third inorganic fine particles being 0.3 to 3% by weight relative to the quantity of the toner particles.

20 Claims, 1 Drawing Sheet

NON-MAGNETIC MONO-COMPONENT DEVELOPER

This application is based on application No. Hei 9-354880 filed in Japan, the contents of which are hereby incorporated by reference.

BACKGROUND OF THE INVENTION

1. Field of the Invention

The present invention relates to a developer for developing an electrical latent image in electrophotography and electrostatic printing, and more particularly to a non-magnetic mono-component developer.

2. Description of the Prior Art

Generally, a two-component developing system and a mono-component developing system are known for developing apparatuses. From the standpoints of prevention of deterioration of chargeabiity and size reduction of an image-forming apparatus, the mono-component developing system has often been employed.

The mono-component developing system is classified into a magnetic mono-component system and a non-magnetic mono-component system. The magnetic mono-component developing system usually requires addition of black magnetic powder to the toner. Therefore, the non-magnetic mono-component developing system can be advantageously employed in a full-color image-forming apparatus. In the non-magnetic mono-component developing system, a developer-regulating member is disposed so as to contact against a developer-supporting member to permit the non-magnetic mono-component developer to pass through a clearance between the developer supporting ember and the developer-regulating member, so that a toner thin layer is formed on the supporting member and the toner is electrically charged at the same time. The thin layer of the charged toner is transported as it is to a developing region in which the electrostatic latent image formed on an electrostatic latent image-support member is developed by the toner.

Generally, a toner is added with inorganic fine particles (externally) as a fluidizing agent, such as silica and titania. For example, Japanese Patent Laid-Open Application No. Hei 7-43930 discloses a non-magnetic mono-component toner which is externally added with a hydrophobic silica and a hydrophobic titanium oxide having a mean particle size of 0.02 to 0.5 $\mu$m, a hydrophobicity of 20 to 95%, and an optical transmission of not less than 40% at 400 nm. In the mono-component developing system, however, because toner particles are forced to pass through the clearance (regulating portion) between the developer-supporting member and the developer-regulating member so as to be electrically charged, some stress is exerted upon the toner particles in the electrical charging process. With the technique described in the above cited publication, it is difficult to satisfactorily solve the problem of deterioration of fluidity which will occur when the toner is repeatedly used. Another problem is that as the fluidizing agent is buried in the toner surface, the surface conditions of the toner will change, it being thus difficult to maintain stably the properties of the toner.

SUMMERY OF THE INVENTION

The object of the present invention is to provide a non-magnetic mono-component developer which is much less liable to any change in the surface conditions of the toner even when copying process is repeated and is able to maintain its toner characteristics, and which has high durability.

In order to accomplish the above object there is provided a non-magnetic mono-component developer comprising:

toner particles containing at least a binder resin and a coloring agent and having a volume mean particle size D of 4 to 10 $\mu$m;

first inorganic fine particles having a mean primary particle size of 1 to 40 nm, the quantity of addition of the first inorganic fine particles being 0.1 to 2% by weight relative to the quantity of the toner particles;

second inorganic fine particles having a mean primary particle size of 40 to 100 nm and not less than 10 nm larger than the first inorganic fine particles, the quantity of addition of the second inorganic fine particles being 0.1 to 2.5% by weight relative to the quantity of the toner particles, the total quantity of addition of the first and second inorganic fine particles being 0.8 to 3% by weight relative to the quantity of the toner particles; and third inorganic fine particles having a mean primary particle size of 100 nm to 1000 D/16 nm and not less than 10 nm larger than the second inorganic fine particles, the quantity of addition of the third inorganic fine particles being 0.3 to 3% by weight relative to the quantity of the toner particles.

DETAILED DESCRIPTION OF THE INVENTION

Figure 1:
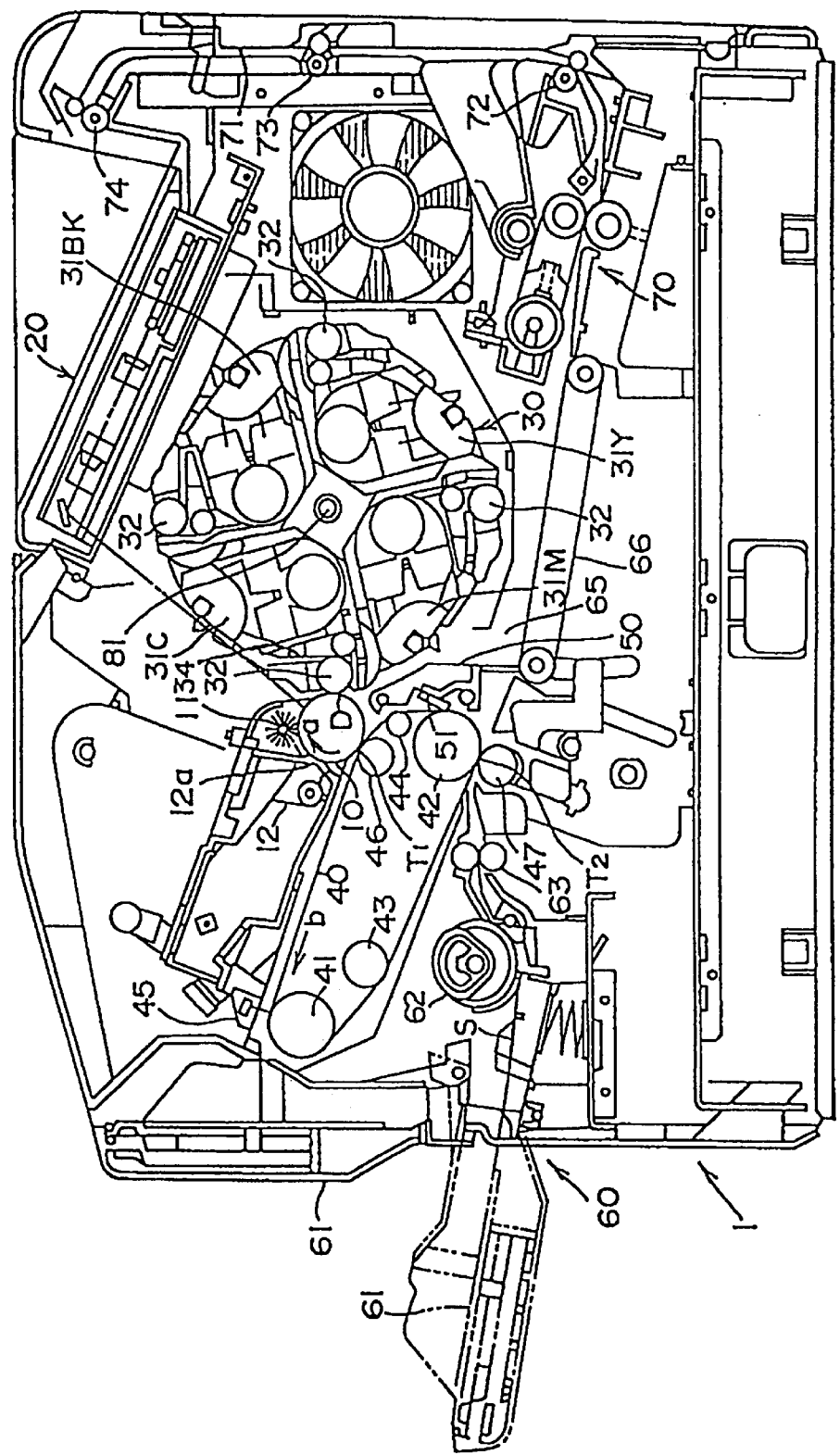
FIG. 1 is a schematic view of a full-color image-forming apparatus.

The present invention relates to a non-magnetic mono-component developer comprising:

toner particles containing at least a binder resin and a coloring agent and having a volume mean particle size D of 4 to 10 $\mu$m;

first inorganic fine particles having a mean primary particle size of 1 to 40 nm, the quantity of addition of the first inorganic fine particles being 0.1 to 2% by weight relative to the quantity of the toner particles;

second inorganic fine particles having a mean primary particle size of 40 to 100 nm and not less than 10 nm larger than the first inorganic fine particles, the quantity of addition of the second inorganic fine particles being 0.1 to 2.5% by weight relative to the quantity of the toner particles, the total quantity of addition of the first and second inorganic fine particles being 0.8 to 3% by weight relative to the quantity of the toner particles; and third inorganic fine particles having a mean primary particle size of 100 nm to 1000 D/16 nm and not less than 10 nm larger than the second inorganic fine particles, the quantity of addition of the third inorganic fine particles being 0.3 to 3% by weight relative to the quantity of the toner particles.

In the present specification, for the mean primary particle size of inorganic fine particles, a mean long span value is shown on the basis of microscopic observations of samples conducted by using a scanning electron microscope (JSM-840A; made by Nippon Denshi K.K.). The volume mean particle size of toner particles is a value based on measurements made by using a Coulter multisizer (made by Coulter Counter K.K.) with an aperture diameter set at 100 $\mu$m.

In the present invention, specific quantities of smaller size particles (first inorganic fine particles), median size particles (second inorganic fine particles), and larger size particles (third inorganic fine particles) are externally added to conventional toner particles. By externally adding such particles of different particle sizes it has now become possible to provide a non-magnetic mono-component developer which is much less liable to unfavorable toner surface change even when copying process is repetitively carried out, so that the developer can maintain its toner characteristics and can exhibit high durability.

First inorganic fine particles contained in the developer of the present invention have a mean primary particle size of from 1 to 40 nm, preferably from 5 to 35 nm, more preferably 5 to 30 nm. When fine particles are contained in the developer to uniformly cover the toner particles, it is possible to obtain desired uniform fluidity of toner. If the mean primary particle size is less than 1 nm, the charging stability of the toner in long term use and/or against environmental change will become insufficient. If the mean primary particle size is more than 40 nm, the effect of such fine particles for fluidity enhancement will decrease. In such a case, in order to achieve desired fluidity, a large amount of fine particles are required, resulting in poor efficiency, which in turn causes a difficulty in the formation of a toner thin layer by the developer-regulating member.

For the first inorganic fine particles, various materials which have been conventionally used as fluidizing agents may be used. For example, silica, alumina, titania (titanium dioxide), tin oxide, magnesium oxide, and zinc oxide are exemplified. These materials may be used alone or in a mixture of two or more kinds. Materials preferable for the first inorganic fine particles are silica and titania.

In the present invention, the first inorganic fine particles are preferably surface-treated with a hydrophobicizing agent. Such a treatment is to maintain environmental stability of the toner, more particularly to inhibit change in toner charge due to humidity. It is desirable that the degree of hydrophobicity is 30 to 80%, preferably 40 to 80%. If the degree of hydrophobicity is lower than 30%, the toner is liable to become deteriorated in its environmental resistance. If the degree of hydrophobicity exceeds 80%, it is difficult to produce stably such particles as have so high hydrophobicity.

Materials usable as hydrophobicizing agents in the present invention include, for example, silane coupling agents, titanate coupling agents, silicone oils, silicone varnishes, and other conventionally used ones. Among these materials, silane coupling agents and silicone oils are preferred. More preferably, silane coupling agents are used. Examples of silane coupling agents include trimethylsilane, trimethyl chlorosilane, dimethyl dichlorosilane, methyltrichlorosilane, allyl dimethyl chlorosilane, benzyl dimethylchlorosilane, methyl trimethoxysilane, methyl triethoxysilane, isobutyl trimethoxysilane, n-hexyl trimethoxysilane, dimethyl dimethoxysilane, dimethyl diethoxysilane, trimethyl methoxysilane, hydroxypropyl trimethoxysilane, phenyl trimethoxysilane, n-hexadecyl trimethoxysilane, n-octyl trimethoxysilane, n-octadecyl trimethoxysilane, vinyl triethoxysilane, (v-methacryloxypropyl trimethoxysilane, and vinyl triacetoxysilane.

Examples of silicone oils are exemplified by dimethyl polysiloxane, methylhydrogen polysiloxane, and methyl phenyl pclysiloxane.

The hydrophobicizing agent may be used in such a quantity as to enable aforesaid hydrophobicity, and according to a conventional method.

In the present invention, the first inorganic fine particles may be surface-treated in combination with a fluoro-silane coupling agent or fluoro-silicone oil. The reason for this is that where the toner is negatively chargeable, such a surface treatment is effective for enhancing the negative chargeability of the toner to prevent image fogging. Generally, chargeability of the toner has been controlled by having toner particles contain a charge controlling agent therein. In the mono-component developing system of the present invention, however, electrical charging of the toner is carried out through frictional charging which will occur when the toner passes through a clearance formed between a developer-supporting member and the developer regulating member. Therefore, the charging capability of surface of toner particles is important for the purpose of toner charging. Hence, in order to control toner charging, it is more effective to adjust the charging characteristics of the external additive to toner rather than adjusting the content of charge-controlling agent contained in toner.

As fluoro-silane coupling agents, the following may be exemplified. These materials may be used alone or in the form of a mixture. It is understood, however, that materials usable as such are not limited to the following.

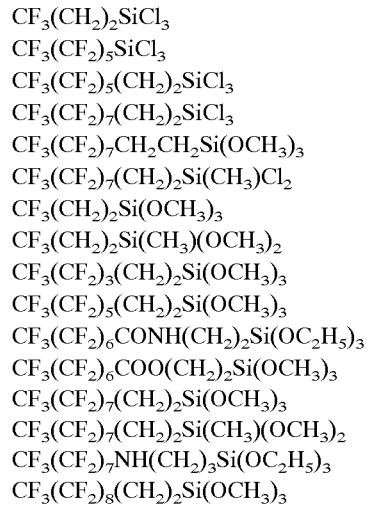

The fluoro-silane coupling agent is used in an amount of 1 to 20 parts by weight, preferably 2 to 15 parts by weight, relative to 100 parts by weight of inorganic fine particles.

Surface treatment of the inorganic fine particles with such a surface treating agent (fluorine-coupling agents, hydrophobicizing agents) may be carried out, for example, by a dry method which includes the steps of diluting the surface treating agents with a solvent, adding the diluted solution to the inorganic fine particles for mixing them together, heating and drying the mixture, then pulverizing the dried mixture, or by a wet method which includes the steps of dispersing the inorganic fine particles in an aqueous solvent to give a slurry, admixing the surface treating agents with the slurry, heating and drying the mixture, then pulverizing the dried mixture. In particular, from the view points of uniformity of surface treatment of the inorganic fine particles by the hydrophobicizing agent and prevention of agglomerationof inorganic fine particle, it is desirable that after hydrophobicizing treatment is carried out in an aqueous solution, surface treatment with a fluorine coupling agents is carried out by using the dry method.

It is desirable that the first inorganic fine particles as an external additive in the present invention are contained in the toner particles in an amount of 0.1 to 2.0% by weight, preferably 0.3 to 1.5% by weight. If the quantity of the first inorganic fine particles is less than 0.1% by weight, the desired fluidity cannot be obtained, and this will be a cause of white lines formed in copied images. If the quantity is more than 2.0% by weight, there may occur a spot-like adhesion of toner components to a photosensitive member. In the relationship between first inorganic fine particles and second inorganic fine particles, it is desirable that a total quantity of the first and second inorganic fine particles contained in the developer is 0.8 to 3.0% by weight, preferably 1.0 to 2.7% by weight. If the total content of the first and second inorganic fine particle is less than 0.8% by weight, the desired fluidity cannot be obtained. If the total content is more than 3.0% by weight, the fluidity of the toner is made excessively high, resulting in reduced electrostatic charging of the toner by the developer-regulating member and/or increased possibility of adhesion of liberated inorganic fine particles to the developer-supporting member. This will be also a cause of a spot-like toner component adhesion to the photosensitive member.

Second inorganic fine particles contained in the developer of the present invention have a mean primary particle size of 40 to 100 nm, preferably 40 to 70 nm, more preferably 45 to 60 nm, and are not less 10 nm larger in mean primary particle size than the first inorganic fine particles. Therefore, when one of the first and second inorganic fine particle materials has a mean primary particle size of 40 nm, whether particles having such a mean primary particle size should be regarded as first inorganic fine particles or as second inorganic fine particles is determined depending upon the mean primary particle size of the other inorganic fine particles. For example, when inorganic fine particles having a mean primary particle size of 15 nm and those having a mean primary particle size of 40 nm are used, the 15 nm particles are regarded as first inorganic fine particles and the 40 nm particles are regarded as second inorganic fine particles. When particles having a mean primary particle size of 40 nm and those having a mean primary particle size of 50 nm are used, the 40 nm particles are regarded as first inorganic fine particles and the 50 nm particles are regarded as second inorganic fine particles.

Second inorganic fine particles would be required in a very large quantity if used in an attempt to cover the toner particles by the second inorganic fine particles alone in order to enhance the fluidity of the toner. This, in turn, makes it difficult to carry out thin layer formation by the developer-regulating member during developing operation. Such problems can be solved by using the second inorganic fine particles in combination with the first inorganic fine particles. By using the second inorganic fine particles in such a way it is possible to reduce the possibility of first inorganic fine particles being buried into toner particles which has been a problem in the prior art. In other words, second inorganic fine particles have a function to control fluidity and reduce any possible unfavorable surface change of toner particles, such as embedment of first inorganic fine particles into toner particles, thereby to secure the desired fluidity.

If the mean primary particle size of second inorganic fine particles is less than 40 nm, the effect of slacken the embedment of first inorganic fine particles into toner particles is substantially reduced. If the mean primary particle size is more than 100 nm, the dispersibility of the second inorganic fine particles in toner particles is noticeably reduced, resulting in reduced toner fluidity. This, in turn, results in deterioration of the follow-up characteristics of the developer as required in relation to the developer-supporting member and may easily lead to the occurrence of a density difference between the upper and lower end portions of a copy image. If the difference in particle size between the second inorganic fine particles and the first inorganic fine particles is less than 10 nm, it is difficult to obtain the preventive effect of the second inorganic fine particles against the embedment of first inorganic fine particles.

For use as second inorganic fine particles, as in the case of first inorganic fine particles, various materials which have been conventionally used as a fluidizing agent may be mentioned as such. Such materials may be used singly or in combination of two or more kinds. Preferred materials for use as second inorganic fine particles are silica and titania.

In the present invention, it is preferable that the second inorganic fine particles are surface-treated with a hydrophobicizhng agent and/or a fluoro-silane coupling agent as in the case of the first inorganic fine particles.

For use as an external additive in the present invention, it is desirable that second inorganic fine particles are contained in the developer in an amount of 0.1 to 2.5% by weight, preferably 0.3 to 2.0% by weight relative to the toner particles. If the quantity of the second inorganic fine particles is less than 0.1% by weight, the effect of such fine particles for slackening the embedment of the first inorganic fine particles cannot be obtained. If the quantity is more than 2.5% by weight, second inorganic fine particles liberated from the toner may easily adhere to the developer-regulating member and/or developer-supporting member, which in turn will cause toner component adhesion and/or a white line appearing in copied images. In the relationship of the second inorganic fine particles and the first inorganic fine particles, it is desirable that the total quantity of the first and second inorganic fine particles is within aforementioned quantity range.

Third inorganic fine particles contained in the developer of the present invention have a mean primary particle size of 100 to 1000 D/16 nm (in which "D" refers to a volume mean particle size ($\mu$m) of toner particles), preferably 125 to 1000 D/18 nm, more preferably 140 nm to 1000 D/20 nm, and are not less 10 nm larger in mean primary particle size than the second inorganic fine particles. When such inorganic fine particles are contained in the developer and are allowed to adhere to toner particles, the possibility of individual toner particles being brought into contact with one another is reduced, and any external stress caused by regulation by the developer-regulating member during a developing operation and stirring in a developing device is diffused, so that the surface of toner particles will not directly be subject to any adverse effect of the external stress. Further, the third inorganic fine particles have a function to enhance the function of the second organic fine particles for slackening the embedment of first inorganic fine particles and also have a function to directly prevent the embedment of first and second inorganic particles into toner particles.

If the mean primary particle size of third inorganic fine particles is less than 100 nm, the possibility of individual toner particles going into contact with one another will increase and adverse effect of external stress is directly exerted on the surface of toner particles, with the result that the third inorganic fine particles cannot exhibit their functions mentioned above. If the mean primary particle size exceeds 1000 D/16 nm, adhesion of third inorganic fine particles to toner particles is rendered difficult, with the result that almost all third inorganic fine particles are separated from toner particles to form agglomerates. As a consequence, such agglomerates will accumulate at the developer-regulating member to cause unsatisfactory control, thus adversely affecting copied images.

For use as third inorganic fine particles, as in the case of first inorganic fine particles, various materials which have been conventionally used as a fluidizing agent may be used as such. Such materials may be used singly or in combination of two or more kinds. Preferred materials for use as third inorganic fine particles are titania, alumina, silica, strontium titanate, barium titanate, zinc oxide, tin oxide, cerium oxide, magnesium zirconate, strontium zirconate, calcium zirconate, and barium zirconate.

Organic/inorganic composite particles having a resin layer formed on the surface of such inorganic fine particle as mentioned above are also usable as third inorganic fine particles.

In the present invention, the third inorganic fine particles may be surface-treated with a hydrophobicizing agent in the same manner as in the case of the first inorganic fine particles.

In the present invention, it is desirable that the third inorganic fine particles, as an external additive, are contained in the developer in a quantity of 0.3 to 3.0% by weight, preferably 0.3 to 2.0% by weight. If the quantity of the third inorganic fine particles is less than 0.3% by weight, the possibility of contact of individual particles becomes high, so that unfavorable effect of external stress is directly exerted on the surface of toner particles, with the result that the third inorganic fine particles cannot exhibit their functions mentioned above. If the quantity of the third inorganic fine particles exceeds 3.0% by weight, accumulation of separated fine particles occurs at the regulating member to cause unsatisfactory control, thus adversely affecting copied images.

The first, second and third inorganic fine particles described above are externally added to toner particles obtained by a method known in the art. Toner particles to be used in the present invention contain at least a binder resin and a coloring agent.

Binder resins usable in the present invention are not particularly limited, but include, for example, styrenic resins, acrylic resins, styrene-acrylic resins, polyamide resins, polyester resins, polyurethane resins, epoxy resins, and other known resins. These resins may be used singly or in combination, being suitably selected according to the use. For example, it is desirable to use a polyester resin for a negatively chargeable toner, a polyester resin for a full-color toner, and a polyester resin or styrene-acrylic resin for a black toner.

In the present invention, a preferred polyester resin is a polyester resin produced by polycondensation reaction of an alcohol component and an acid component, wherein the alcohol component is bisphenol A alkylene oxide adduct and the acid component is a phthalo-dicarboxylic acid or a combination of a phthalo-dicarboxylic acid and an aliphatic dicarboxylic acid.

For the bisphenol A alkylene oxide adduct, bisphenol A propylene oxide adduct and bisphenol A ethylene oxide are preferred. Preferably, these materials are used in combination.

As the alcohol component, a small amount of such a diol or polyhydroxy alcohol as mentioned below may be used together with the bisphenol A alkylene oxide adduct. Examples of such alcohol component include diols, such as ethylene glycol, diethylene glycol, triethylene glycol, 1,2-propylene glycol, 1,3-propylene glycol, 1,4-butanediol, and neopentyl glycol; sorbitol, 1,2,3,6-hexanetetrol, 1,4-sorbitan, pentaerythritol, dipentaerythritol, tripentaerithritol, 1,2,4-butanetriol, 1,2,5-pentanetriol, glycerol, 2-methylpropanetriol, 2-methyl-1,2,4-butanetriol, trimethylolethane, trimethylolpropane, and 1,3,5-trihydroxyrnethyl benzene.

For the phthalo-dicarboxylic acid, materials usable as such include, for example, terephthalic acid, isophthalic acid and their anhydrides or lower alkyl esters thereof.

For the aliphatic dicarboxylic acid usable in combination with the phthalo-dicarboxylic acid include, for example, fumaric acid, maleic acid, succinic acid, alkyl- or alkenylsuccinic acid having 4–18 carbon atoms, and their anhydrides or lower alkyl esters thereof.

Where toner particles of the present invention are used as a full-color toner, preferred binder resins are those having a glass transition point of 55–75° C., preferably 58–70° C., a softening point of 95–120° C., preferably 100–118° C., and a number mean molecular weight of 2,500–6,000, preferably 3,000–5,500, a ratio of weight mean molecular weight/number mean molecular weight of 2–8, preferably 3–7. If the glass transition point is lower, the heat resistance of the toner is lowered. If the glass transition point is higher, the light transmission and color-mixture characteristics of the toner are lowered. If the softening point becomes low, a high-temperature offset may easily occur during a fixing operation. If the softening point becomes higher, the fixing strength becomes lower. If the number-mean molecular weight is small, peeling-off of toner may easily occur when the image is folded. If the number-mean molecular weight becomes larger, the fixing strength is lowered. If the ratio of weight-mean molecular weight/number-mean molecular weight is small, a hightemperature offset may easily occur. If the ratio becomes larger, the light transmittance is lowered.

For the binder resin, from the standpoint of improvement of dispersibility of colorant in the binder resin, it is desirable to use those having an acid value of 1.0 to 30.0 KOH mg/g, preferably 1.0 to 25.0 KOH mg/g, more preferably 2.0 to 20.0 KOH mg/g. If the acid value is less than 1.0 KOH mg/g, the effect of dispersion improvement is reduced. If the acid value becomes higher than 30.0 KOH mg/g, the negative chargeability of the toner is intensified, which in turn leads to increased changes in the quantity of charge due to environmental changes.

When preparing a polyester resin as mentioned above, for the purpose of adjusting the acid value of the resin, a polyvalent carboxylic acid, such as trimellitic acid, or the like, may be used in such a small amount as will not adversely affect the light-transmission capability of the toner. Materials usable as such a polyvalent carboxylic acid component include, for example, 1,2,4-benzene tricarboxylic acid (trimellitic acid), 1,2,5-benzene tricarboxylic acid, 2,5,7-naphthalene tricarboxylic acid, 1,2,4-naphthalene tricarboxylic acid, 1,2,4-butane tricarboxylic acid, 1,2,5-hexane tricarboxylic acid, 1,3-dicarboxyl-2-methyl-2-methylene carboxypropane 1,2,4-cyclohexane tricarboxylic acid, tetra (methylene carboxyl) methane, 1,2,7,8-octane tetracaboxylic acid, pyromellitic acid, and anhydrides and lower alkyl esters thereof.

For the coloring agent, various kinds of known colorants may be used, including cyan, magenta, yellow, and black. For the quantity of such colorants, same quantity values as conventionally used may be applied. Usually, colorants are added in an amount of about 1 to 15 parts by weight relative to 100 parts by weight of the binder resin.

Additives other than above mentioned colorants, such as charge controlling agent and offset-preventing agent, may be added as required.

For the charge controlling agent, zinc salicylate complex and other known charge controlling agents may be used, and the kind of such agent to be used may be selected according to the intended purpose. For the purpose of full-color copying, it is desirable to use a colorless or light yellow charge controlling agent. For black color copying there is no particular color limitation. The usage of the charge controlling agent may be suitably set according to the intended purpose, but usually the charge controlling agent is used in a quantity range of 0.1 to 10 parts by weight, preferably 0.5 to 5.0 parts by weight, relative to 100 parts by weight of the binder resin.

The kind of the offset-preventing agent is not particularly limited. Examples of usable offset-preventing agents are polyethylene wax, oxidized polyethylene wax, polypropylene wax, oxidized polypropylene wax, carnauba wax, sazol wax, rice wax, candelilla wax, jojoba oil, and beeswax. The use of such an agent can not only improve the anti-offset characteristicas of the developer, but also can reduce the trouble of toner adhesion to the developer-regulating member and/or developer-supporting member in a non-magnetic, mono-component developing device. In particular, it is desirable to use a wax having an acid value of 0.5 to 30 KOH mg/g from the viewpoint of dispersion in the binder resin having such an acid value as above mentioned. An addition amount of such a wax is 0.5 to 5 parts by weight, preferably 1 to 4 parts by weight, relative to 100 parts by weight of the binder resin. If the amount is less than 0.5 parts by weight, the effect of the wax addition is insufficient. If the wax addition is more than 5 parts by weight, light transmission and color reproducibility are insufficient.

Toner particles of the present invention can be produced by means of any known method, such as kneading/pulverizing method, suspension polymerization method, emulsion polymerization method, emulsion dispersion method, or encapsulation method, by using above described binder resin, coloring agents, and other desired additives. Among these methods, the kneading/pulverizing method is preferred for use in the preparation of toner particles, from the view points of production cost and production stability.

The kneading/pulverizing method comprises the steps of mixing toner components, such as resin and colorants, in a mixing apparatus, such as Henschel mixer, melting and kneading the resulting mixture, pulverizing the kneaded mixture into coarse particles after cooling, pulverizing the coarse particles finely, and classifying the pulverized fine particles. The toner particles of the invention are produced through these steps so that they have a volume mean particle size of 4 to 10 μm, preferably 6 to 9 μm.

Toner particles thus obtained are mixed with aforementioned first inorganic fine particles, second inorganic fine particles, and third inorganic fine particles, to give a non-magnetic, mono-component developer.

The non-magnetic mono-component developer of the invention as obtained in this way can be used either as a developer for full-color image-forming or as a developer for black image-forming by suitably selecting colorants, binder resin, charge controlling agent, and/or wax. In the present invention, however, the developer is more advantageous for use as a full-color developer. Therefore, while the developer of the present invention is usable in any developing device adopting a mono-component developing system, it is especially desirable to use the developer in a full-color image-forming machine. One example of full-color image-forming machines is described below with reference to FIG. 1.

In FIG. 1, a full-color laser beam printer is composed fo a photosensitive drum 10 driven to rotate in the direction of arrow a, a laser-scanning optical system 20, a full-color developing device 30, an endless intermediate transfer belt 40 driven to rotate in the direction of arrow b, and a sheet feeder 60. Around the photosensitive drum 10 there are installed a charging brush 11 for charging the surface of the photosensitive drum 10 to a predetermined potential, and a cleaner 12 equipped with a cleaner blade 12a for removing a toner residue existing on the photosensitive drum 10.

The laser-scanning optical system 20 is a well-known system incorporating a laser diode, a polygon mirror, and an fθ optical device, and has a control portion to which respective printing data in C (cyan), M (magenta), Y (yellow), and Bk (black) colors are transmitted from a host computer. The laser-scanning optical system 20 sequentially output printing data for each respective color in the form of laser beam and the photosensitive drum 10 is scanned for exposure, so that static latent images for respective colors are sequentially formed on the photosensitive drum 10.

The full-color developing device 30 is an assembly integrally formed of four developing units 31C, 31M, 31Y and 31BK for different colors, in which non-magnetic, mono-component toners of C, M, Y and BK are accommodated respectively. The full-color developing device 30 is rotatable clockwise with a support shaft 81 as a rotation center. Each developing unit is equipped with a developing sleeve (developer-supporting member) 32 and a toner-regulating blade (developer-regulating member) 34. Toner transported through rotation of the developing sleeve 32 is electrically charged as it passes through a pressure contact portion (regulating portion) between the blade 34 and the developing sleeve 32.

The intermediate transfer belt 40 is strained in an endless fashion about support rollers 41, 42 and tension rollers 41, 42 and is driven to rotate in the direction of arrow b in synchronous relation with the photosensitive drum 10. At a side of the intermediate transfer belt 40 there is provided a projection (not shown) such that image-forming operations, such as exposure, development, and transfer, are controlled through detection of the projection by a microswitch 45. A freely rotatable first transfer roller 46 is pressed against the intermediate transfer belt 40 to be brought into contact with the photosensitive drum 10. The spot of this contact is a first transfer portion $T_1$. Further, the intermediate transfer belt 40, at a portion supported by the support roller 42, is in contact with a freely rotatable second transfer roller 47. The spot of this contact is a second transfer portion $T_2$.

A cleaner 50 is installed in a space between the developing device 30 and the intermediate transfer belt 40. The cleaner 50 has a blade 51 for removing toner residue on the intermediate transfer belt 40. The blade 51 and the second transfer roller 47 are movable toward and away from the intermediate transfer belt 40.

The sheet feeder 60 is constituted of a feed tray 61 openable on the front side of the image-forming apparatus body 1, a feed roller 62, and a timing roller 63. Recording sheets S, placed on the feed tray 61, are fed one by one through the rotation of the feed roller 62 in the rightward direction in the drawing and are transported to the second transfer portion by the timing roller 63 in synchronous relation with images formed on the intermediate belt 40. A horizontal transport path 65 for recording sheets is constituted of an air suction belt 66, including the sheet feed portion, and from a fixing device 70 there extends a vertical transport path 71 provided with transport rollers 72, 73, 74. Record sheets S are discharged from the vertical transport path 71 onto the upper portion of the image-forming apparatus body 1.

In conjunction with the foregoing, printing operation of the full-color printer will be explained.

When printing operation starts, the photosensitive drum 10 and the intermediate transfer belt 40 are driven to rotate at same peripheral speed, and photosensitive drum 10 is electrically charged by the charging brush 11 to a predetermined potential.

Subsequently, exposure of cyan image is carried out by the laser-scanning optical system 20 so that an electrostatic latent image of cyan image is formed on the photosensitive drum 10. The electrostatic latent image is immediately developed by a developing unit 31C, and the resulting toner image is transferred onto the intermediate transfer belt 40 at the first transfer portion. Immediately after the end of first transfer, the developing unit 31M is switched to the developing section D. The exposure, development, and first transfer of magenta image are carried out. Then, the developing unit is switched to the developing unit 31Y, exposure, development, and first transfer of yellow image are carried out. Further, the developing unit is switched to the developing unit 31Bk, exposure, development, and first transfer of black image are carried out. In this way, toner images are placed one over another on the intermediate transfer belt 40.

Upon completion of the final first transfer, the record sheet S is fed to the second transfer section, and a full-color toner image is transferred onto the recording sheet S. Upon completion of the second transfer, recording sheet S is transported to a belt-type contact heat-fixing unit 70 to fix the full-color toner images on the record sheet S. The record sheet S is discharged onto the upper portion of the printer body 1.

The following examples are given to illustrate the present invention in further detail.

EXAMPLES

Methods of preparation of polyester resins A-C used in the following examples are described below.

Preparation of Polyester Resin A (for Color Toner)

Into a 4-necked glass-made flask equipped with a thermometer, a stirrer, a flow-down type condenser, and a nitrogen inlet pipe were charged polyoxypropylene(2,2)-2,2-bis(4-hydroxyphenyl)propane, polyoxyethylene(2,2)-2,2-bis(4-hydroxyphEnyl)propane and terephthalic acid in a molar ratio of 5:5:9.5. After a polymerization initiator (dibutyl tin oxide) was added, the contents were caused to react in a mantle heater with stirring at 220° C. in a nitrogen atmosphere. As a result, a polyester resin A having a number-mean molecular weight (Mn) of 4,800, weight-mean molecular weight (Mn)/number-mean molecular weight 4.5, a softening point of 108° C., glass transition point of 66° C. and an acid value (AV) of 4.2 KOH mg/g was obtained.

Preparation of Polyester Resin B (for Black Toner)

Into a 4-necked glass-made flask equipped with a thermometer, a stirrer, a flow-down type condenser, and a nitrogen inlet pipe were charged polyoxypropylene(2,2)-2,2-bis(4-hydroxyphenyl)propane, polyoxyethylene(2,2)-2,2-bis(4-hydroxyphenyl) propane, isododecenyl succinic anhydride, terephthalic acid, and fumaric acid in a weight ratio of 82:77:16:32:30. After a polymerization initiator (dibutyl tin oxide) was added, the contents were caused to react in a mantle heater with stirring at 220° C. in a nitrogen atmosphere. As a result, a polyester resin B having a softening point of 110° C., a glass transition point of 60° C. and an acid value (AV) of 17.5 KOH mg/g was obtained.

Preparation of Polyester Resin C (for Black Toner)

Styrene and 2-ethylhexyl acrylate were put at a weight ratio of 17:3.2, together with dicumyl peroxide, a polymerization initiator, into a flow-down type funnel. Into a 4-necked glass-made flask equipped with a thermometer, a stirrer, a flow-down type condenser, and a nitrogen inlet pipe were charged, polyoxypropylene(2,2)-2,2-bis(4-hydroxyphenyl)propane, polyoxyethylene(2,2)-2,2-bis(4-hydroxyphenyl)propane, isododecenyl succinic anhydride, terephthalic acid, 1,2,4-benzene tricarboxylic anhydride, and acrylic acid which were prepared in a weight ratio of 42:11:11:11:8:1, together with a polymerization initiator (dibutyl tin oxide). Styrene, etc. were introduced dropwise while the contents of the flask were stirred in a nitrogen atmosphere at 135° C. Thereafter, the temperature was raised to 230° C. to allow reaction of the contents. As a result, a polyester resin C having a softening point of 150° C., a glass transition point of 62° C. and an acid value of 24.5 KOH mg/g was obtained.

Molecular weight measurements were made by using permeation chromatography (807-IT type; made by Nikko Bunko Kogyo K.k.), with tetrahydrofuran used as a carrier solvent, and converted in terms of polystyrene.

Measurements of softening points were made by using a flow tester (CFT-500, made by Shimazu Seisakusho K.k.); and with samples of 1.0 g each, a die of 1.0 mm×1.0 mm was used under the conditions: heating-up rate, 3.0° C./min; load, 30 kg. The temperature at which one half of the sample flowed out was taken as softening point.

Measurements of glass transition point were made using a differential scanning calorimeter (DSC-200; made by Seiko Denshi K.k.) with respect to weighed samples of 10 mg each. Alumina was used as reference. A shoulder value of main endothermic peaks within a range of 30–80° C. was taken as the glass transition point.

For acid value, a weighed sample was dissolved in a suitable solvent, and measurements were expressed in terms of mg of potassium hydroxide necessary for neutralizing acid radicals by using an indicator, such as phenolphthalein.

In the present examples, the following inorganic fine particles were used:

Inorganic fine particles A (hydrophobic silica, hydrophobicity 55%, mean primary particle size, 7 nm; TS500; made by Cabosil K.k.);

Inorganic fine particles B (hydrophobic silica, hydrophobicity 48%, mean primary particle size, 15 nm; R974, made by Nippon Aerosil K.k.);

Inorganic fine particles C (hydrophobic silica, hydrophobicity 55%, mean primary particle size, 50 nm; R809; made by Nippon Aerosil K.k.);

Inorganic fine particles D (hydrophobic titanium dioxide (rutile), hydrophobicity 55%, mean primary particle size, 15 nm; MT-150W; made by Teika K.k.), surface treated with n-hexyltrimethoxysilane);

Inorganic fine particles E (hydrophobic titanium dioxide (anatase), hydrophobicity 60%, mean primary particle size, 50 nm; surface treated with n-hexylmethoxysilane);

Inorganic fine particles F (hydrophobic titanium dioxide (anatase), hydrophobicity 57%, mean primary particle size, 50 nm; surface treated with n-hexylmethoxysilane);

Inorganic fine particles a (titanium dioxide, mean primary particle size 250 nm; KR-380; made by Chitan Kogyo K.k.);

Inorganic fine particles b (titanium dioxide, mean primary particle size 150 nm; KR-480; made by Chitan Kogyo K.k.);

Inorganic fine particles c (synthetic spherical silica, mean primary particle size 200 nm; SO-C1; made by Admatechs K.k.);

Inorganic fine particles d (organo-inorganic composite particles, mean primary particle size 300 nm);

Inorganic fine particles e (synthetic spherical silica, mean primary particle size 1 $\mu$m; SO-C3; made by Admatechs K.k.);

Inorganic fine particles f (titanium dioxide, mean primary particle size 1.5 $\mu$m, KR-310DS; made by Chitan Kogyo K.k.);

Inorganic fine particles g (strontium titanate, mean primary particle size 250 nm).

In the above connection, it is to be noted that the inorganic fine particle d was prepared in the following way. First, a solution composed of 36 g of vinyl trimethoxysilane, 120 g of methanol, and 0.2 g of polymerization initiator (2,2-azobis(2.4-dimethyl valeronitryle)) was added to an aqueous mixed solution of 38 g of 25 wt % amrmonia water and 1,722 g of water. A hydrolysis-condensation reaction of vinyl trimethoxysilane was carried out. Then, the solution was heated to a temperature of 70–75° C. in a nitrogen atmosphere and kept for 2 hours. Polymerization of vinyl groups was carried out. After cooling, vacuum drying was carried out at 50° C. Thus, aforesaid inorganic particles d were obtained. The particles had a $SiO_2$ content of 73 wt %.

For measurement of hydrophobicity, 50 ml of pure water was put in a 200-ml beaker, and 0.2 g of sample was added. A methanol dehydrated with anhydrous sodium sulfate was added from a buret. The point of time at which the sample disappeared almost entirely from the liquid surface was taken as the terminal point, and hydrophobicity was calculated on the basis of the quantity of methanol required until that point and according to the following equation:

Hydrophobicity=((methanol quantity used/(50+methanol quantity used))×100.

The molten blend polypropylene wax used in the present examples was prepared according to the following method.

Preparation of Molten Blend Polypropylene Wax

A non-oxidized polypropylene wax having an acid value of 0 KOH mg/g ("Viscol 550P"; made by Sanyo Kasei Kogyo K.k.) and an oxidized polypropylene wax having an acid value of 52 KOH mg/g ("Yumex 1010", made by Sanyo Kasei Kogyo K.k.) were mixed in a weight ratio of 92:8. After melted and kneaded, the mixture was cooled and pulverized. As a result, a molten blend polypropylene wax having a melting viscosity of 205 cps and a softening point of 150° C. was obtained.

Example 1

Polyester resin A and cyan pigment (C. I. pigment blue 15-3) were put at a weight ratio of 7:3 into a pressure kneader and were kneaded therein. The kneaded mixture was cooled and pulverized by a feather mill to give a pigment master batch.

Ninety three parts by weight of polyester resin A, 10 parts by weight of aforesaid master batch, 2 parts by weight of polypropylene wax ("Viscol" TS200; made by Sanyo Kasei Kogyo K.k.; acid value, 3.5 KOH mg/g), and 1.5 parts by weight of zinc salicylate complex (E84; made by Orient Kagaku Kogyo K.k.) were thoroughly mixed in a ball mill. The mixture was melt-kneaded in a twin-screw extruding-kneader. Thereafter, the kneaded material was cooled, then pulverized into coarse particles in a feather mill. The coarse particles were pulverized finely in a jet mill and classified. As a result, toner particles having a volume mean particle size of 8.0 μm mean were obtained.

To 100 parts by weight of the toner particles thus obtained were added 0.5 parts by weight of inorganic fine particles A, 1.0 part by weight of inorganic fine particles F, and 1.0 part by weight of inorganic fine particles a, and the materials were mixed in a ball mill. Thus, a developer was obtained.

Examples 2–19 and Comparative Examples 1–8

Developers were obtained in the same way as in Example 1, except that inorganic fine particles shown in Tables 1 and 2 were used in such quantities as shown.

Example 20

Toner particles having a volume mean particle size of 6.1 μm were prepared and a developer was obtained in the same way as in Example 1, except that the above toner particles were used.

Example 21

Forty parts by weight of polyester resin B, 60 parts by weight of polyester resin C, 1 part by weight of polyethylene wax (800P; made by Mitsui Sekiyu Kagaku Kogyo K.k.; melting viscosity at 160° C., 5400 cps, softening point, 140° C.), 3 parts by weight of molten blend polypropylene wax, 8 parts by weight of acid carbon black ("Mogul L; made by Cabot K.k.; pH 2.5; mean primary particle size 24 nm), and 2.5 parts by weight of zinc salicylate complex (E84; made by Orient Kagaku Kogyo K.k.) were thoroughly mixed in a Henschel mixer, and the mixture was melt-kneaded in a twin-screw extruding-kneader (PCM 30; Ikegai Tekko K.k.). Thereafter, the kneaded material was cooled, then pulverized into coarse particles in a hammer mill. The coarse particles were pulverized finely in a jet mill and classified to give toner particles having a volume mean particle size of 8.2 μm mean.

To 100 parts by weight of toner particles thus obtained were added 0.5 parts by weight of inorganic fine particles A, 0.5 parts by weight of inorganic fine particles F, and 1.0 part by weight of inorganic fine particles a, and the materials were mixed in a ball mill. Thus, a developer was obtained.

Evaluation

Each developer obtained in manner as above described was loaded in an electrophotographic printer equipped with non-magnetic mono-component developing device (SP1000, made by Minolta K.k.) which was so reconstructed as to be variable with respect to pressure of the regulating blade, with setting made to produce a character pattern of a B/W ratio of 5% under ordinary temperature and humidity conditions (25° C., 45%). The developer was evaluated with respect to "white line" and "follow-up characteristics", which will be described hereinafter, and on the basis of the following criteria. Evaluation was made with respect to copy images at initial stage (after 10 sheets copying) and after 3,000 sheets copying.

White Line

A half tone image of A4 size was copied. With respect to copied images, observation was made as to the occurrence of white lines, and with respect to a thin layer formed on the developing sleeve, observation was made as to the occurrence of any irregular line on the layer. Evaluation was made according to the following ranking standards.

◯: No irregular line occurred in the toner thin layer on the sleeve, and no white line occurred in the copied images.

Δ: Irregular lines occurred slightly in the toner thin layer on the sleeve, but no white line occurred in the copied images; no problem for practical use.

X: Irregular lines occurred in the toner thin layer on the sleeve, and white lines occurred in the coped images.

In evaluation after copying of 3,000 sheets, the following ranking standard was added.

XX: Toner was spilling from the regulating portion and/or side seal portion.

Follow-up

A black solid image of A4 size was copied, and the density of the copy image at upper and lower portions was visually observed, and evaluation was ranked as the following.

○: No density difference; excellent in density uniformity.

Δ: Slight density difference and/or inuniform density, but no problem for practical purposes.

X: Considerable density difference and/or thin spots observed; a problem from the view point of practical use.

The evaluation results are shown in the following Tables 1 and 2, together with treating conditions in the foregoing Examples and Comparative Examples.

TABLE 1

| | Toner | Inorganic Fine Particle | | | | | | Evaluation | | | |
|---|---|---|---|---|---|---|---|---|---|---|---|
| | | Particle size, 1–40 nm | | Particle size, 40–100 nm | | Particle size, 100 nm–1000D/16 nm | | Initial | | After 3000 copies | |
| Example | Particle Size D (μm) | Kind (particle size (nm)) | Quantity of addition (wt %) | Kind (particle size (nm)) | Quantity of addition (wt %) | Kind (particle size (nm)) | Quantity of addition (wt %) | White line | Follow-up | White line | Follow-up |
| Example 1 | 8.0 | A (7) | 0.5 | F (50) | 1.0 | a (250) | 1.0 | ○ | ○ | ○ | ○ |
| Example 2 | 8.0 | A (7) | 0.5 | F (50) | 1.0 | b (150) | 1.0 | ○ | ○ | ○ | ○ |
| Example 3 | 8.0 | A (7) | 0.5 | F (50) | 1.0 | c (200) | 1.0 | ○ | ○ | ○ | ○ |
| Example 4 | 8.0 | A (7) | 0.5 | F (50) | 1.0 | d (300) | 1.0 | ○ | ○ | ○ | ○ |
| Example 5 | 8.0 | A (7) | 0.5 | F (50) | 1.0 | a (250) | 0.5 | ○ | ○ | ○ | ○ |
| Example 6 | 8.0 | A (7) | 0.5 | F (50) | 1.0 | a (250) | 2.0 | ○ | ○ | Δ | ○ |
| Example 7 | 8.0 | A (7) | 0.5 | C (50) | 2.0 | a (250) | 1.0 | ○ | ○ | ○ | ○ |
| Example 8 | 8.0 | B (15) | 0.6 | C (50) | 1.0 | a (250) | 1.0 | ○ | ○ | ○ | ○ |
| Example 9 | 8.0 | D (15) | 1.0 | C (50) | 1.0 | a (250) | 1.0 | ○ | ○ | ○ | Δ |
| Example 10 | 8.0 | E (20) | 1.5 | C (50) | 0.5 | a (250) | 1.0 | ○ | ○ | Δ | Δ |
| Example 11 | 8.0 | D (15) | 1.0 | F (50) | 1.0 | c (200) | 1.0 | ○ | ○ | ○ | ○ |
| Example 12 | 8.0 | A (7) | 1.0 | F (50) | 0.5 | a (250) | 1.9 | ○ | ○ | ○ | ○ |
| Example 13 | 8.0 | A (7) | 0.5 | F (50) | 1.5 | a (250) | 1.0 | ○ | ○ | ○ | ○ |
| Example 14 | 8.0 | A (7) | 0.5 | F (50) | 1.0 | g (250) | 1.0 | ○ | ○ | ○ | ○ |
| Example 15 | 8.0 | A (7) | 0.5 | F (50) | 1.0 | g (250) | 0.5 | ○ | ○ | ○ | ○ |
| Example 16 | 8.0 | A (7) | 0.5 | F (50) | 1.0 | g (250) | 2.0 | ○ | ○ | ○ | ○ |
| Example 17 | 8.0 | A (7) | 0.5 | C (50) | 2.0 | g (250) | 1.0 | ○ | ○ | ○ | ○ |
| Example 18 | 8.0 | B (15) | 0.6 | C (50) | 1.0 | g (250) | 1.0 | ○ | ○ | ○ | ○ |
| Example 19 | 8.0 | A (7) | 0.5 | C (50) | 1.5 | g (250) | 1.0 | ○ | ○ | ○ | ○ |
| Example 20 | 6.1 | A (7) | 0.5 | F (50) | 1.0 | a (250) | 1.0 | ○ | ○ | ○ | Δ |
| Example 21 | 8.2 | A (7) | 0.5 | F (50) | 0.5 | a (250) | 1.0 | ○ | ○ | ○ | ○ |

TABLE 2

| | Toner | Inorganic Fine Particle | | | | | | | | Evaluation | | | |
|---|---|---|---|---|---|---|---|---|---|---|---|---|---|
| | | Particle size, 1–40 nm | | Particle size, 40–100 nm | | Particle size, 100 nm–1000D/16 nm | | Other | | Initial | | After 3000 copies | |
| Comparative Example | Particle Size D (μm) | Kind (particle size (nm)) | Quantity of addition (wt %) | Kind (particle size (nm)) | Quantity of addition (wt %) | Kind (particle size (nm)) | Quantity of addition (wt %) | Kind (particle size (nm)) | Quantity of addition (wt %) | White line | Follow-up | White line | Follow-up |
| Comparative Example 1 | 8.0 | — | — | C (50) / F (50) | 1.0 / 1.0 | a (250) | 1.0 | — | — | Δ | x | — | — |
| Comparative Example 2 | 8.0 | A (7) | 0.5 | F (50) | 1.0 | — | — | e (1000) | 1.0 | Δ | ○ | x x | x |
| Comparative Example 3 | 8.0 | A (7) | 0.5 | F (50) | 1.0 | — | — | f (1500) | 1.0 | Δ | ○ | x | x |
| Comparative Example 4 | 8.0 | B (15) | 0.6 | F (50) | 1.0 | — | — | — | — | ○ | ○ | x | x |
| Comparative Example 5 | 8.0 | B (15) / D (15) | 0.6 / 1.0 | — | — | — | — | — | — | ○ | ○ | x x | x |
| Comparative Example 6 | 8.0 | B (15) / D (15) | 0.6 / 1.0 | F (50) | 1.0 | — | — | — | — | ○ | ○ | x | x |
| Comparative Example 7 | 8.0 | B (15) | 0.2 | F (50) | 0.4 | a (250) | 1.0 | — | — | Δ | ○ | — | — |
| Comparative Example 8 | 8.0 | B (15) | 0.6 | F (50) | 1.0 | a (250) | 5.0 | — | — | x | x | — | — |

From the evaluation results, it was found that no white line occurred on the copy image and good follow-up characteristics were demonstrated. The evaluation results also tell that the developer of the invention has high durability and high fluidity.

With respect to Comparative Examples 1, 7 and 8, dusting and/or toner spill occurred during the process of copying, and copying was interrupted; therefore, the above mentioned evaluation after 3000 sheets copying was not carried out. Such a trouble may be attributable to poor fluidity due to absence of smaller particles corresponding to first inorganic fine particles in the case of Comparative Example 1; to unsatisfactory fluidity due to too small total addition of first and second fine particles in the case of Comparative Example 7; and to separation of fine particles due to an excessive addition of larger size fine particles in the case of Comparative Example 8. Conceivably, in the case of Comparative Examples 2 and 3, since the particle size of larger size fine particles is so large that such fine particles will easily be separated due to repeated copying operation and will accumulate in the regulating section, and this causes unfavorable effect on copied images. In the case of Comparative Examples 4 to 6, it is conceivable that fluidity drop could not be avoided due to absence of larger size fine particles, and therefore that the follow-up characteristics were lowered, which resulted in adverse affection on copid images. Further, toner spill and/or dusting was found in the vicinity of side seal portion. In the case of Comparative Example 5, fluidity drop was noticeable due to the absence of medium size fine particles in addition to larger size fine particles, and this further degraded copied images.

In accordance with the present invention, it is possible to provide a developer which is less liable to surface-changes of the toner and is able to maintain its toner characteristics even after repetition of copying process. Further, the toner of the present invention is excellent in durability.

What is claimed is:

1. A non-magnetic mono-component developer comprising:
    toner particles containing at least a binder resin having an acid value of 1 to 30 KOH mg/g, a wax having an acid value of 0.5 to 30 KOH mg/g and a coloring agent and having a volume mean particle size D of 4 to 10 μm;
    first inorganic fine particles having a mean primary particle size of 1 to 40 nm, the quantity of addition of the first inorganic fine particles being 0.1 to 2% by weight relative to the quantity of the toner particles;
    second inorganic fine particles having a mean primary particle size of 40 to 100 nm and not less than 10 nm larger than the first inorganic fine particles, the quantity of addition of the second inorganic fine particles being 0.1 to 2.5% by weight relative to the quantity of the toner particles, the total quantity of addition of the first and second inorganic fine particles being 0.8 to 3% by weight relative to the quantity of the toner particles; and
    third inorganic fine particles having a mean primary particle size of 100 nm to 1000 D/16 nm and not less than 10 nm larger than the second inorganic fine particles, the quantity of addition of the third inorganic fine particles being 0.3 to 3% by weight relative to the quantity of the toner particles.

2. A non-magnetic mono-component developer as defined in claim 1, wherein the mean primary particle size of the first inorganic fine particles is 5 to 35 nm, the mean primary particle size of the second inorganic fine particles is 40 to 70 nm, and the mean primary particle size of the third inorganic fine particles is 125 nm to 1000 D/18 nm.

3. A non-magnetic mono-component developer as defined in claim 1, wherein the mean primary particle size of the first inorganic fine particles is 5 to 30 nm, the mean primary particle size of the second inorganic fine particles is 45 to 60 nm, and the mean primary particle size of the third inorganic fine particles is 140 nm to 1000 D/20 nm.

4. A non-magnetic mono-component developer as defined in claim 1, wherein the quantity of addition of the first inorganic fine particles is 0.3 to 1.5% by weight relative to the quantity of the toner particles, the quantity of addition of the second inorganic fine particles is 0.3 to 2% by weight relative to the quantity of the toner particles, and the quantity of addition of the third inorganic fine particles is 0.3 to 2% by weight relative to the quantity of the toner particles.

5. A non-magnetic mono-component developer as defined in claim 1, wherein the first inorganic fine particles are surface-treated with a hydrophobicizing agent.

6. A non-magnetic mono-component developer as defined in claim 5, wherein the degree of hydrophobicity of the first inorganic fine particles is 30 to 80%.

7. A non-magnetic mono-component developer as defined in claim 5, wherein the first inorganic fine particles are surface-treated with a fluoro-silane coupling agent.

8. A non-magnetic mono-component developer as defined in claim 1, wherein the second inorganic fine particles are surface-treated with a hydrophobicizing agent.

9. A non-magnetic mono-component developer as defined in claim 8, wherein the degree of hydrophobicity of the second inorganic fine particles is 30 to 80%.

10. A non-magnetic mono-component developer as defined in claim 8, wherein the second inorganic fine particles are surface-treated with a fluoro-silane coupling agent.

11. A non-magnetic mono-component developer as defined in claim 1, wherein the third inorganic fine particles are at least one kind of inorganic fine particles selected from the group consisting of titania, alumina, silica, strontium titanate, barium titanate, zinc oxide, tin oxide, cerium oxide, magnesium zirconate, strontium zirconate, calcium zirconate, and barium zirconate.

12. A non-magnetic mono-component developer as defined in claim 1, wherein the third inorganic fine particles are at least one kind of inorganic fine particles selected from the group consisting of titania, silica and strontium titanate.

13. A non-magnetic mono-component developer as defined in claim 1, wherein the third inorganic fine particles are strontium titanate.

14. A negatively chargeable non-magnetic mono-component developer for use in a full-color image-forming apparatus, comprising:
    negatively chargeable toner particles containing at least a binder resin having an acid value of 1 to 30 KOH mg/g, a wax having an acid value of 0.5 to 30 KOH mg/g and a coloring agent and having a volume mean particle size D of 4 to 10 μm;
    first inorganic fine particles having a mean primary particle size of 1 to 40 nm, a quantity of addition of the first inorganic fine particles being 0.1 to 2% by weight relative to the quantity of the toner particles;
    second inorganic fine particles having a mean primary particle size of 40 to 100 nm and not less than 10 nm larger than the first inorganic fine particles, a quantity of addition of the second inorganic fine particles being 0.1 to 2.5% by weight relative to the quantity of the toner particles, the total quantity of addition of the first and second inorganic fine particles being 0.8 to 3% by weight relative to the quantity of the toner particles; and third inorganic fine particles having a mean primary particle size of 100 nm to 1000 D/16 nm and not less than 10 nm larger than the second inorganic fine particles, a quantity of addition of the third inorganic fine particles being 0.3 to 3% by weight relative to the quantity of the toner particles.

15. A negatively chargeable non-magnetic mono-component developer as defined in claim 14, wherein the binder resin has an acid value of 1 to 25 KOH mg/g.

16. A negatively chargeable non-magnetic mono-component developer as defined in claim 14, wherein the binder resin has a glass transition point of 55 to 75° C., a softening point of 95 to 120° C., a number-mean molecular weight of 2,500 to 6,000, and 2 to 8 of Mw/Mn (weight mean molecular weight/number mean molecular weight).

17. A negatively chargeable non-magnetic mono-component developer as defined in claim 15, wherein the toner particles contain 0.5 to 5 parts by weight of a wax having an acid value of 0.5 to 30 KOH mg/g the wax relative to 100 parts by weight of the binder resin.

18. A negatively chargeable non-magnetic mono-component developer as defined in claim 14, wherein the volume mean particle size of the toner particles is 6 to 9 :m, the mean primary particle size of the first inorganic fine particles is 5 to 35 nm, the mean primary particle size of the second inorganic fine particles is 40 to 70 nm, and the mean primary particle size of the third inorganic fine particles is 125 nm to 1000 D/18 nm.

19. A negatively chargeable non-magnetic mono-component developer as defined in claim 14, wherein the volume mean particle size of the toner particles is 6 to 9 :m, the mean primary particle size of the first inorganic fine particles is 5 to 30 nm, the mean primary particle size of the second inorganic fine particles is 45 to 60 nm, and the mean primary particle size of the third inorganic fine particles is 140 nm to 1000 D/20 nm.

20. A negatively chargeable non-magnetic mono-component developer as defined in claim 14, wherein the quantity of addition of the first inorganic fine particles is 0.3 to 1.5% by weight relative to the quantity of the toner particles, the quantity of addition of the second inorganic fine particles is 0.3 to 2% by weight relative to the quantity of the toner particles, and the quantity of addition of the third inorganic fine particles is 0.3 to 2% by weight relative to the quantity of the toner particles.

* * * * *